United States Patent [19]

Herrington et al.

[11] Patent Number: 5,330,534
[45] Date of Patent: Jul. 19, 1994

[54] KNEE JOINT PROSTHESIS WITH INTERCHANGEABLE COMPONENTS

[75] Inventors: Stephen M. Herrington, Warsaw, Ind.; Adolph V. Lombardi, Jr., Columbus; Bradley K. Vaughn, Worthington, both of Ohio

[73] Assignee: Biomet, Inc., Warsaw, Ind.

[21] Appl. No.: 832,927

[22] Filed: Feb. 10, 1992

[51] Int. Cl.$^5$ .............................. A61F 2/38
[52] U.S. Cl. ........................ 623/20; 623/18
[58] Field of Search .................. 623/18, 20

[56] References Cited

U.S. PATENT DOCUMENTS

| | | |
|---|---|---|
| 3,694,821 | 10/1972 | Moritz . |
| 3,798,679 | 3/1974 | Ewald . |
| 3,837,009 | 9/1974 | Walker . |
| 3,840,905 | 10/1974 | Deane . |
| 4,034,418 | 7/1977 | Jackson et al. . |
| 4,094,017 | 6/1978 | Matthews et al. . |
| 4,209,861 | 7/1980 | Walker et al. . |
| 4,213,209 | 7/1980 | Insall et al. . |
| 4,298,992 | 11/1981 | Burstein et al. . |
| 4,340,978 | 7/1982 | Buechel et al. . |
| 4,470,158 | 9/1984 | Pappas et al. . |
| 4,714,472 | 12/1987 | Averill et al. . |
| 4,888,021 | 12/1989 | Forte et al. ............ 623/20 |
| 4,892,547 | 1/1990 | Brown . |
| 5,007,932 | 4/1991 | Bekki et al. ............ 623/18 |
| 5,007,933 | 4/1991 | Sidebotham et al. . |
| 5,147,405 | 9/1992 | Van Zile et al. . |

OTHER PUBLICATIONS

Greenwald, A. Seth, et al, "Total Knee Replacement", *Knee*, pp. 301-312, 1981.
Blunn, Gordon W., "The Dominance of Cyclic Sliding in Producing Wear in Total Knee Replacements," Clinical Orthopedics and Related Research, pp. 253-260, Dec. 1991.
Draganish, L. F., et al., "Interaction Between Intrinsic Knee Mechanics and the Knee Extensor Mechanism," *Journal of Orthopaedic Research*, 5:539-547, 1984.
"P.F.C. Modular Total Knee System: Cruciate Retaining Tibial Inserts", Johnson & Johnson Orthopaedics brochure (undated).
"P.F.C. Modular Total Knee System": Cruciate Retaining, Femoral Component, Johnson & Johnson Orthopaedics brochure (undated).
Brochure, CINTOR, Division Codman & Shurtleff, Inc., Total Condylar 2 Knee Prosthesis, 1978, 2 pages.
Article, C. G. Attenborough, Inst. Mech. Engrs., Total Knee Replacement Using a Stabilised Gliding Prosthesis, from conference held Sep. 16-18, 1974, pp. 91-95.
P. S. Walker, Human Joints and their Artificial Replacements, 1977 pp. 328-337.
Article, G. Deane, Inst. Mech. Engrs., The Deane Knee a New Concept in Knee Joint Design, 1975, pp. 140-143.
Article, P. S. Walker, Acta Orthopaedica Belgica, Design of a Knee Prosthesis System, 1980, pp. 766-775.
The Journal of Anthroplasty, T. P. Andriacchi, et al., Sep. 1986, Knee Biomechanics and Total Knee Replacement, vol. 1, No. 3, pp. 211-219.

*Primary Examiner*—Paul Prebilic
*Attorney, Agent, or Firm*—Harness, Dickey & Pierce

[57] ABSTRACT

A knee joint prosthesis having independently interchangeable components. The knee joint prosthesis includes a femoral component having a first bearing surface defined at least in part by a first radius in the coronal plane. The femoral component further includes a second bearing surface defined at least in part by a second radius in the coronal plane, the second radius being displaced from the first radius. The distance between the center of the first radius to the center of the second radius is substantially constant and does not depend on the size of the femoral component. The knee joint prosthesis further includes a tibial component which is operable to engage the femoral component.

10 Claims, 4 Drawing Sheets

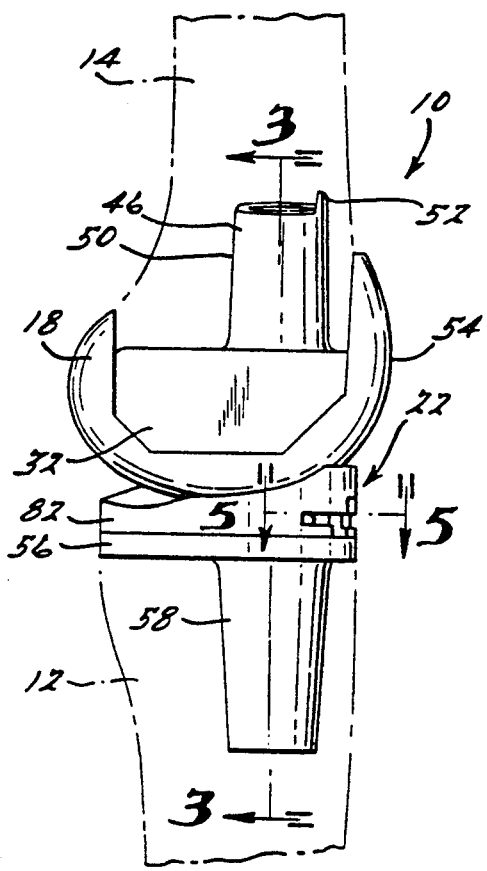
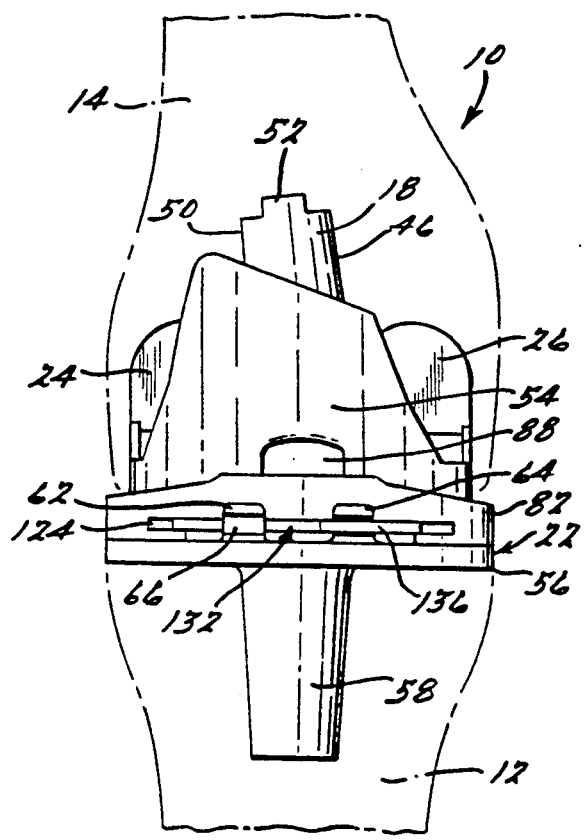
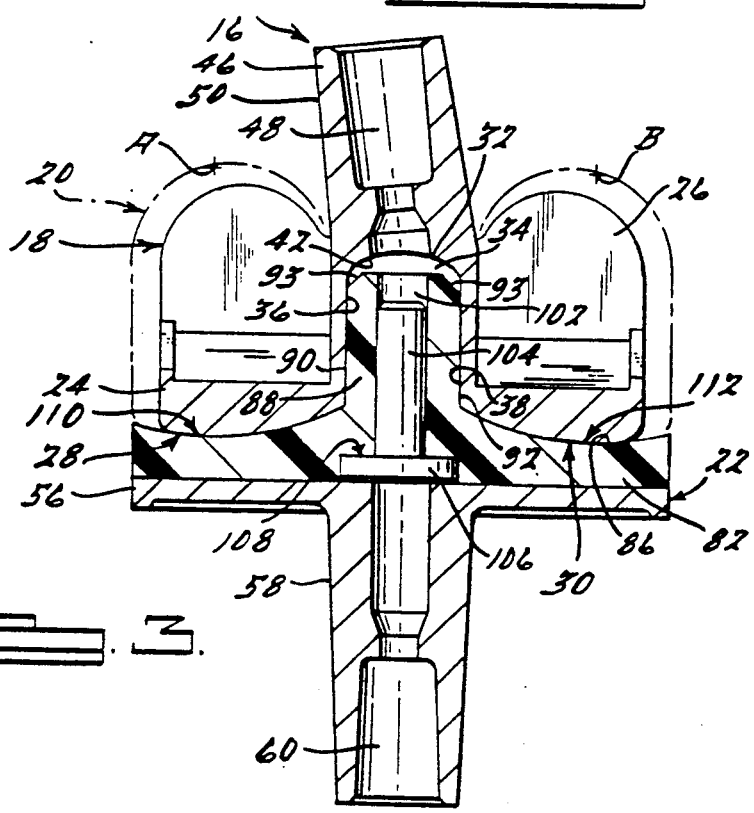

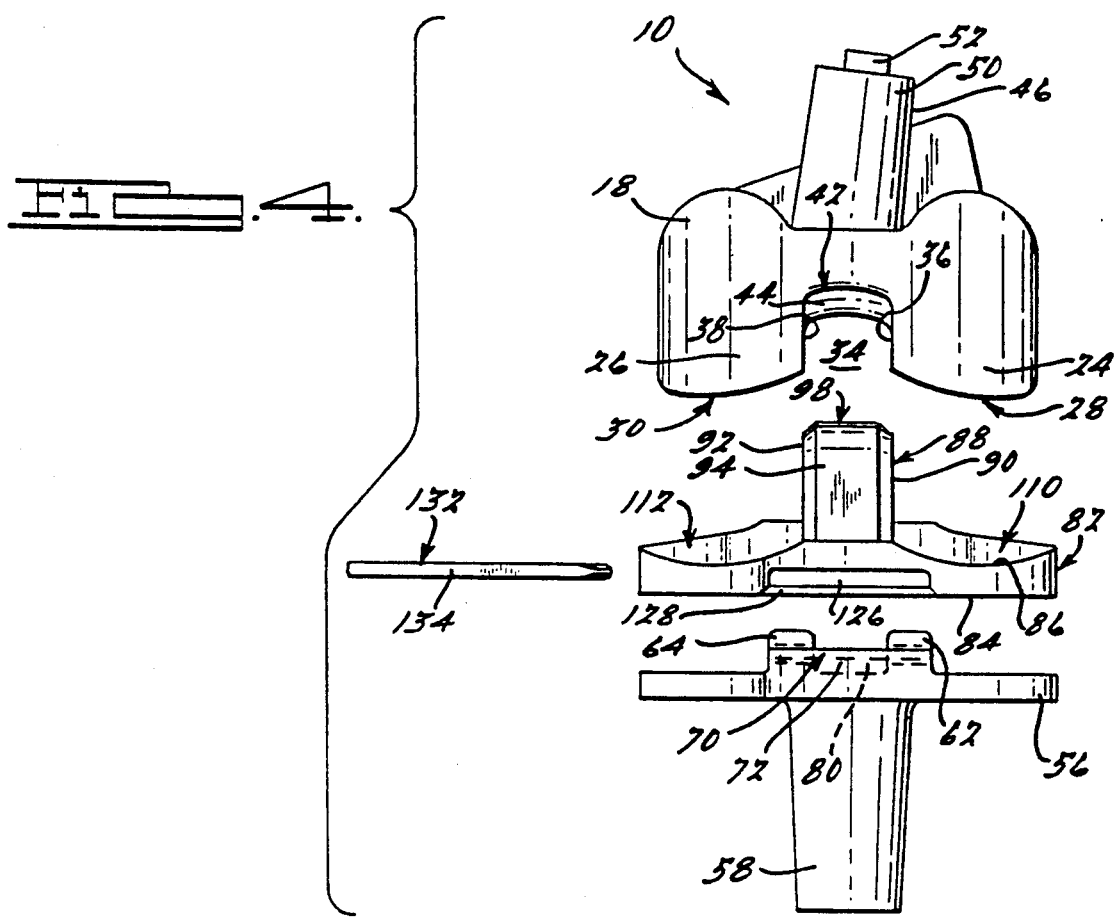
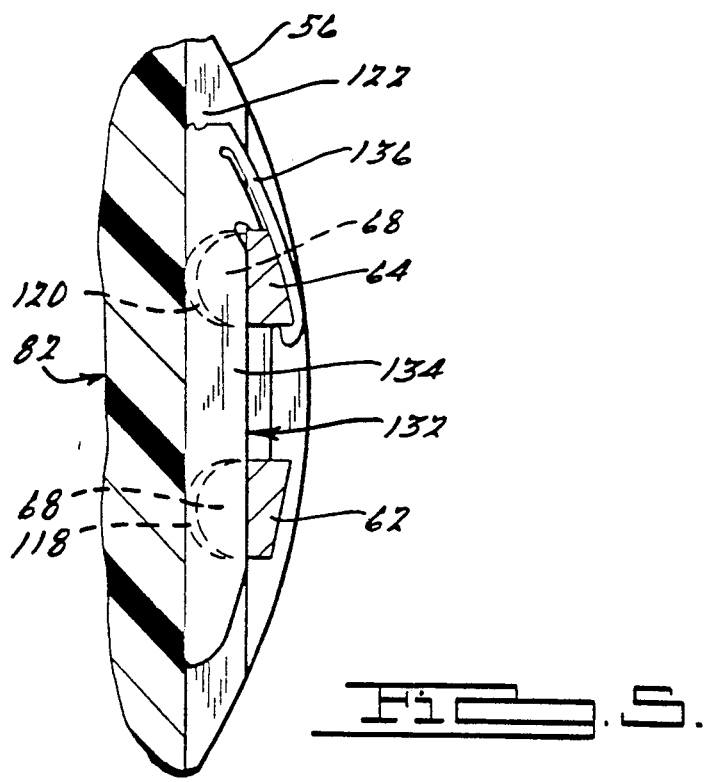

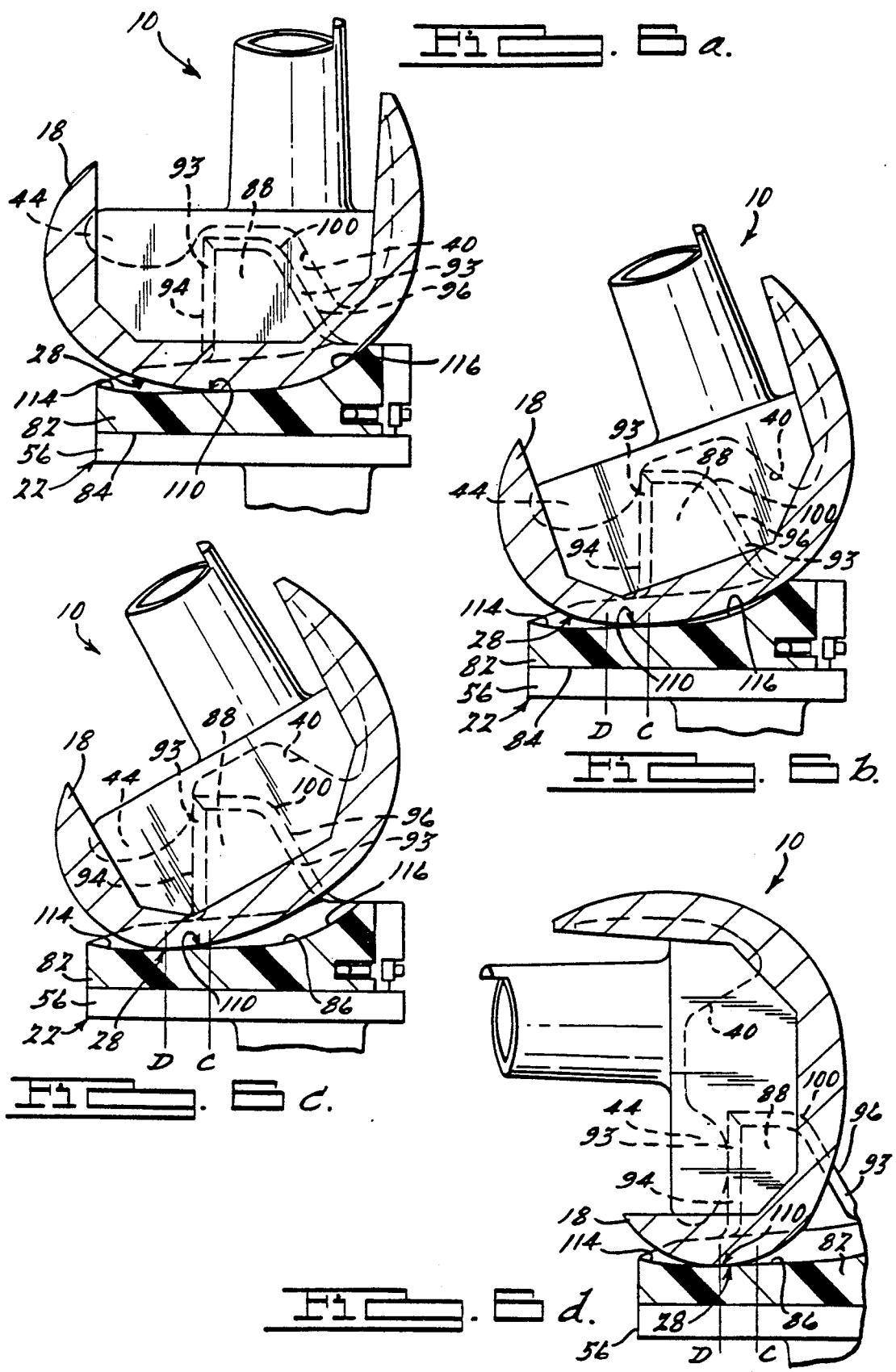

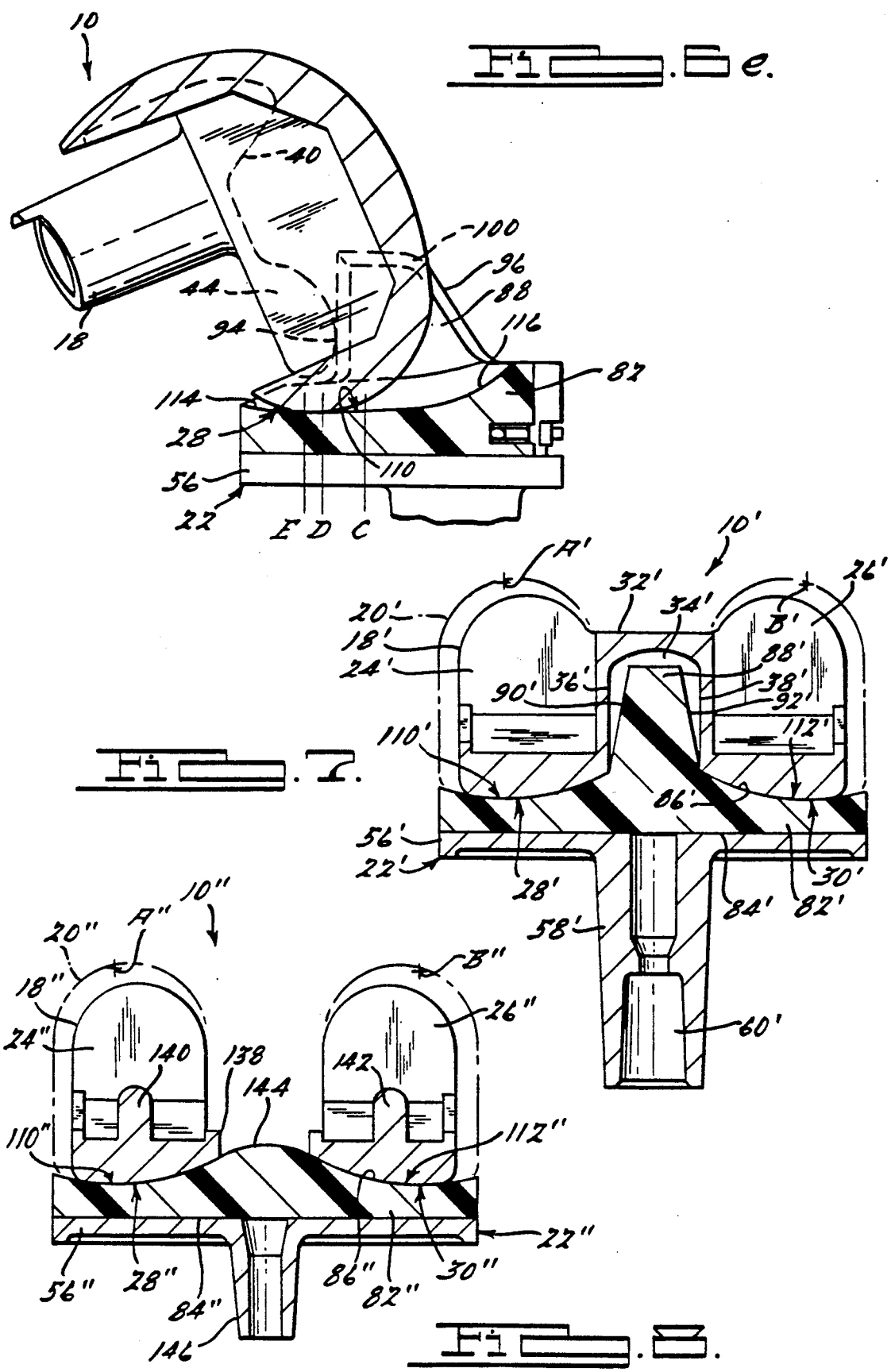

KNEE JOINT PROSTHESIS WITH INTERCHANGEABLE COMPONENTS

BACKGROUND OF THE INVENTION

The present invention relates generally to a knee joint prosthesis which replaces the articulating surfaces of the femur and tibia, and more particularly, to a prosthetic replacement system for a knee having interchangeable femoral and tibial components.

A knee joint prosthesis typically comprises a femoral component and a tibial component. The femoral component and tibial component are designed to be surgically attached to the distal end of the femur and proximal end of the tibia respectively. The femoral component is further designed to cooperate with the tibial component in simulating the articulating motion of an anatomical knee joint.

Motion of a natural knee is kinematically complex. During a relatively broad range of flexion and extension, the articular surfaces of a natural knee experience rotation, medial and lateral angulation, translation in the sagittal plane, rollback and sliding. Knee joint prostheses, in combination with ligaments and muscles, attempt to duplicate natural knee motion as well as absorb and control forces generated during the range of flexion. Depending on the degree of damage or deterioration of the knee tendons and ligaments, however, it may be necessary for a knee joint prosthesis to limit one or more of these motions in order to provide adequate stability.

While knee joint prostheses are effective in replacing the anatomical knee joint, they nevertheless have several disadvantages. For example, surgeons tend to select the size of the knee joint prosthesis by determining which knee joint prosthesis most closely matches the size of both the femur and tibia collectively rather than the size of the femur and tibia individually. This is because knee joint prostheses often lack interchangeability between various sized femoral components and various sized tibial components. Accordingly, the surgeon could not optimally select the size of the tibial component based primarily on the size of the tibia, as well as select the size of the femoral component based primarily on the size of the femur, so as to obtain the best anatomical fit for the prosthesis. In addition, knee joint prostheses sometimes lack interchangeability between a femoral component designed specifically for a right knee or a left knee and a particular tibial component.

In addition, knee joint prostheses often do not reproduce the relatively unconstrained kinematics of the anatomical knee joint. This includes translation of the femoral component in the sagittal plane with respect to the tibial component. Furthermore, such knee joint prostheses often do not permit the extensor moment arm between the patellar ligament and the femoral/tibial contact point to be taken into consideration during the design of a prosthesis. As a result, a noticeable change in the effort required by a patient during movement of the knee joint occurs when a prosthetic knee is compared with the natural knee.

Accordingly, it is desired to provide a knee joint prosthesis which substantially duplicates the motion associated with the anatomical knee joint while providing interchangeability between components.

SUMMARY OF THE INVENTION

Generally, the present invention provides a prosthetic replacement system for a knee having independently interchangeable components, wherein different sized femoral components can engage different sized tibial components. The invention also encompasses a method for replacing the human knee in which the size of the femoral and tibial components are selected independently of each other.

More specifically, the prosthetic replacement system includes a femoral component and a tibial component each of which have a bearing surface. The shape of the bearing surfaces in the coronal plane are selected such that femoral components of different sizes can each operatively engage tibial components of different sizes thereby making the femoral components interchangeable with the tibial components.

In one aspect of the invention, the bearing surfaces of the femoral and tibial components are selected such that the femoral component and the tibial component are operable to maintain line-to-line contact in the coronal plane during a substantial range of flexion. In another aspect of the invention, the femoral and tibial components are operable to substantially maintain the position of the contact area constant during a given range of flexion.

An advantage of the present invention is to provide a knee joint prosthesis in which a tibial component is adapted to engage various sized femoral components.

Another advantage of the present invention is to provide a prosthetic replacement system in which a tibial component is adapted to receive femoral components which are designed for both left and right knee joints.

Another advantage of the present invention is to provide a knee joint prosthesis in which the tibial and femoral components are interchangeable while not requiring tibial insert associated with the tibial component to overhang or underhang the tibial tray of the tibial component.

A further advantage of the present invention is to provide a knee joint prosthesis in which the load bearing surface of the tibial component remains in line-to-line contact in the coronal plane with the femoral component throughout a substantial range of flexion as well as during varus-valgus angulation.

Another advantage of the present invention is to provide a knee joint prosthesis in which the extensor moment arm is proportional to the size of the knee joint prosthesis.

Yet another advantage of the knee joint prosthesis of the present invention is to permit a relatively unconstrained translation of the femoral component in the sagittal plane with respect to the tibial component throughout a range of flexion.

The invention, in one form thereof, provides a prosthetic replacement system for a knee having interchangeable components comprising a femoral component and a tibial component. The femoral component includes dished-condyles in that the femoral component has a first bearing surface which has a cross-section in the coronal plane defined at least in part by a first radius, and a second bearing surface having a cross-section in the coronal plane defined at least in part by a second radius which is displaced from the first radius. The distance between the center of the first radius to the center of the second radius is substantially equal for different sized femoral components.

The invention further provides, in one form thereof, a knee joint prosthesis comprising a femoral component having first means for guiding movement of the femoral component. The knee joint prosthesis further includes a tibial component having second means for guiding the movement of the femoral component which is operable to engage the first means for guiding movement of the femoral component. The knee joint prosthesis is thereby able to maintain the position of the contact area between the femoral component and the tibial component substantially constant during a range of flexion.

BRIEF DESCRIPTION OF THE DRAWINGS

The various advantages of the present invention will become apparent to those skilled in the art after reading the following specification and by reference to the drawings in which:

FIG. 1 is a sagittal elevational view of a right knee joint having a knee joint prosthesis according to the first preferred embodiment of the present invention with the tibia and the femur of the natural knee shown in phantom;

FIG. 2 is a coronal elevational view of the knee joint prosthesis shown in FIG. 1;

FIG. 3 is a partial sectional view taken through the line 3—3 shown in FIG. 1 with a femoral component of larger size shown in phantom;

FIG. 4 is an exploded posterior elevational view of the knee joint prosthesis shown in FIG. 1;

FIG. 5 is a partial sectional view taken through the line 5—5 shown in FIG. 1 illustrating the locking member used in conjunction with the present invention;

FIGS. 6(a) to 6(e) are partial sagittal sectional views of the knee joint prosthesis shown in FIG. 1 illustrating five different positions of the femoral component with respect to the tibial component during a range of flexion from full extension to full flexion;

FIG. 7 is a coronal sectional view of the knee joint prosthesis according to the second preferred embodiment of the present invention with a femoral component of larger size being shown in phantom; and FIG. 8 is a coronal sectional view of the knee joint prosthesis according to the third preferred embodiment of the present invention with a femoral component of larger size being shown in phantom.

DETAILED DESCRIPTION OF THE PREFERRED EMBODIMENTS

Referring now to FIGS. 1 and 2, there is shown a knee joint prosthesis 10 in accordance with the first preferred embodiment of the present invention. The knee joint prosthesis 10 is functionally depicted as being secured to a tibia 12 and a femur 14 of the surgically resected right knee joint, with the tibia 12 and femur 14 being shown in phantom. It will be understood that while the knee joint prosthesis 10 is suited for implantation into a right knee joint, a suitable left knee prosthesis can be similarly constructed.

The knee joint prosthesis 10 is the most constrained embodiment of the present invention and is designed for implantation in knee joints having a severe degree of deterioration and instability. Accordingly, the knee joint prosthesis 10 of the first embodiment prohibits movement of the components of the knee joint prosthesis 10 in the medial-lateral direction throughout a range of flexion. During implantation of the knee joint prosthesis 10, the cruciate ligaments (not shown) and collateral ligaments (not shown) of the natural knee will be typically either functionally compromised or surgically sacrificed.

The knee joint prosthesis 10 of the present invention provides the basis for a prosthetic replacement system 16 having independently interchangeable components as shown in FIG. 3. The prosthetic replacement system 16 comprises a plurality of femoral components 18 and 20 which are operable to replace a portion of the femur 14. The femoral component 20 is slightly larger in size than the femoral component 18 and is therefore suitable for use with a relatively larger femur than is the femoral component 18. The size of the femoral component to be used with the knee joint prosthesis 10 (i.e., the femoral component 18 or the femoral component 20) is selected to most closely fit the size of the femur 14 to which it is to be secured. The prosthetic replacement system 16 further includes a tibial component 22 which is able to replace a portion of the tibia 12. The size of the tibial component 22 is selected to most closely fit the size of the tibia to which it is to be secured.

Because different sized femoral components (e.g., femoral components 18 and 20) are able to operatively engage the tibial component 22, the particular size of the femoral component which is used with a particular knee joint prosthesis 10 can be selected by the surgeon independently of the size of the tibia 12. In addition, the size of the tibial component 22 can be selected by the surgeon independently of the size of the femur 14. Accordingly, the surgeon can optimally select the sizes of the femoral component and the tibial component so as to obtain the best anatomical fit for the knee joint prosthesis 10. The prosthetic replacement system 16 can therefore more easily accommodate a wide variation in the size of the tibia 12 and the femur 14.

The femoral component 18 will now be described in greater detail. It will be appreciated that this discussion applies equally to the femoral component 20. The femoral component 18 is secured to the distal end of the femur 14 after the femur 14 has been resected in a manner which is well known in the art. The femoral component 18 can be constructed in various sizes having overall medial-lateral dimensions ranging from 55 mm to 80 mm in increments of typically 5 mm. The femoral component 18 is unitary in structure and is preferably cast of a biocompatible high-strength alloy such as a cobalt-chromium-molybdenum alloy conforming to ASTM F 75, though other suitable materials may be used. All surfaces which do not contact the femur 14 are preferably highly polished.

The femoral component 18 includes a first condylar portion 24 and a second condylar portion 26 which have a first femoral bearing surface 28 and a second femoral bearing surface 30 respectively. The first femoral bearing surface 28 is defined in the coronal plane by a first radius which has a center (i.e., Point A in FIG. 3) which is approximately 1.5 inches from the first femoral bearing surface 28. Similarly, the second femoral bearing surface 30 is defined in the coronal plane by a second radius which also has a center (i.e., Point B in FIG. 3) which is approximately 1.5 inches from the second femoral bearing surface 30. The distance between the centers of the first radius and the second radius which define the first and second femoral bearing surfaces 28 and 30 is constant between the femoral component 18 and the femoral component 20. That is, the distance between both Point A and Point B is approximately 2.0 inches for both the femoral component 18 and the femoral component 20 as well as for other sizes of femoral components. By maintaining constant the distance between the centers of the radii forming the first and second femoral bearing surfaces 28 and 30 for femoral components of different sizes, the prosthetic replacement system 16 can use different sized femoral components with different sized tibial components. In addition, because the distance between the centers of the radii forming first and second femoral bearing surfaces 28 and 30 and the bearing surfaces 28 and 30 themselves are the same, the tibial component 22 may receive a femoral component which is designed either for a right knee or a left knee.

The first and second condylar portions 24 and 26 of femoral component 18 are interconnected by an intercondylar portion 32 which defines an intercondylar recess 34. The intercondylar portion 32 includes a first lateral sidewall 36 and a second lateral sidewall 38 which are planar and substantially parallel to each other. The distance between the first and second lateral sidewalls 36 and 38 is preferably 0.600 inch. In addition, the tolerance between the first and second lateral sidewalls 36 and 38 is preferably relatively small and may require the use of a precise non-polishing finish such as an Electro-Chemical Mill process. The anterior portions of the first and second lateral sidewalls 36 and 38 are connected by the anterior surface 40 of the intercondylar portion 32 (see FIG. 6). The anterior surface 40 of the intercondylar portion 32 angles anteriorly in an inferior direction at approximately 60° with respect to the superior surface 42 of the intercondylar portion 32.

To provide first means for guiding movement of the femoral component 18 with respect to the tibial component 22, the femoral component 18 further includes a cam portion 44. The cam portion 44 extends between the posterior portions of the first and second condylar portions 24 and 26 and is convexly curved in the sagittal plane. The cam portion 44 guides the movement of the femoral component 18 in such a manner that the femoral component 18 is able to rollback and slide with respect to the tibial component 22 from between approximately 12°–20° of flexion to about 30° of flexion. In addition, the cam portion 44 maintains the position of the contact area on the tibial component 22 substantially constant with respect to the femoral component 18 from approximately 30° of flexion to approximately 90° of flexion. Finally, the cam portion 44 also allows the femoral component 18 to rollback and slide with respect to the tibial component 22 from approximately 90° of flexion to full flexion (i.e., approximately 110°). The movement of the femoral component 18 with respect to the tibial component 22 will be more fully described below.

The shape and location of the cam portion 44 is selected so that the extensor moment arm (i.e., the distance between patellar ligament and the position of the contact area between the femoral component 18 and the tibial component 22 in the sagittal plane) is proportional to the relative size of the knee joint prosthesis 10 at 90° of flexion. That is, the cam portion 44 and the stabilizing post (described below) are shaped in such a manner that their interaction will cause the distance between the patellar ligament and the position of the contact area established by the femoral component 18 on the tibial component 22 to be proportional to the size of the tibial component 22. By making this distance proportional to the size of the tibial component 22, the effort exerted by a patient during flexion and extension of the knee joint prosthesis 10 can more closely approximate the effort required during flexion of a natural knee.

The femoral component 18 further comprises femoral stem boss 46 which extends superiorly approximately 7° from vertical in the coronal plane from the superior surface 42 of the intercondylar portion 32. The femoral stem boss 46 angles slightly toward the lateral side thereby allowing the femoral stem boss 46 to be surgically inserted into the longitudinal center of the femur 14.

The femoral stem boss 46 includes an internal bore 48 which is defined by a tapered cylindrical wall 50. The internal bore 48 of the femoral stem boss 46 is able to receive a suitable support member (not shown) which is secured to the femur 14 in a manner well known in the art. Alternatively, the femoral stem boss 46 and the support member may be unitary in structure. The femoral stem boss 46 further includes an anti-rotation member 52 in the form of a unitary extension of the anteriormost portion of the top of the cylindrical wall 50. The anti-rotation member 52 engages a recess formed within the support member which thereby prevents rotation of the support member.

The femoral component 18 further comprises a patellar portion 54 which is disposed on the anterior surface of the femoral component 18. As those skilled in the art will appreciate, the patellar portion 54 is shaped to allow anatomical tracking of a natural or prosthetic patella. Patella prostheses which are compatible with the present invention may be of varying shapes such as round and dome-shaped, and may be constructed from polyethylene, polyethylene with a metal backing, or other suitable materials. Such patella prostheses may also be of various sizes preferably ranging from 30 mm to 36 mm and may include hexagonal pegs with undercuts located thereon, though other suitable sizes may be used.

The tibial component 22 will now be described in greater detail. The tibial component 22 is adapted to be secured to the proximal end of the tibia 12 after the tibia 12 has been resected in a manner well known in the art. The tibial component 22 includes a platform-like tibial tray 56 and an inferiorly extending tibial stem boss 58. The tibial stem boss 58 is adapted to be received in a corresponding opening (not shown) made by the surgeon in the longitudinal center of the tibia 12. A bore 60 disposed within the tibial stem boss 58 is able to receive a suitable support member (not shown) which is secured to the tibia 12 in a manner well known in the art. If additional affixation is required, through holes (not shown) can be provided in the tibial tray 56 through which bone screws may be passed to secure the tibial tray 56 to the end of the tibia 12. In such circumstances, the upper portions of such holes are countersunk so that the heads of the bone screws fit entirely below the superior surface of the tibial tray 56. Preferably, the tibial tray 56 including the tibial stem boss 58 is machined from wrought Ti-6Al-4V Conforming to ASTM F 36 or forged from Ti-6Al-4V conforming to ASTM F 620 and are unitarily formed in a manner well known in the art. Alternatively, the tibial tray 56 with a permanent support member can be unitarily constructed from a biologically compatible polymer such as ultra-high molecular weight polyethylene (UHMWPE). When the tibial tray 56 is constructed with a permanent support member, the tibial component 22 does not include the tibial stem boss 58. The tibial tray 56 can be constructed of different sizes having an overall medial-lateral dimension ranging from 59 mm to 91 mm preferably in increments of 4 mm.

The tibial tray 56 further includes a pair of integrally formed posts 62 and 64 which extend superiorly at the anterior edge of the tibial tray 56. The posts 62 and 64 are positioned equally spaced from either side of the center of the implant in the sagittal plane. The anterior surface of each of the posts 62 and 64 includes an anterior horizontal groove 66, while the posterior surface of each of the posts 62 and 64 includes a posterior horizontal groove 68. The anterior horizontal groove 66 and the posterior horizontal groove 68 operate to receive a locking bar 132 which is able to secure a tibial insert 82 to the tibial tray 56 in a manner more fully described below.

The tibial tray 56 also includes a unitarily formed posterior projection 70 which extends superiorly from the posterior portion of the tibial tray 56. The posterior projection 70 has a posterior side 72 which conforms with the posterior edge of the tibial tray 56 and an anterior side which has a horizontal channel 80. The horizontal channel 80 is used to engage a recess formed in the tibial insert 82 in a manner described below.

The tibial component 22 further includes the tibial insert 82. The tibial insert 82 is symmetrical about the sagittal plane thereby permitting the tibial insert 82 to be used with femoral components which are designed either for the left or the right knee. The superior surface 86 of the tibial insert 82 is formed to posteriorly slope downwardly at a 3° angle so as to facilitate resection of the tibia 12. This is because the tibia 12 is often resected with a posterior slope to increase the range of flexion, though such slope is difficult for the surgeon to form. The thickness of the tibial insert 82 can be varied as is necessary for a particular implantation. Preferably, the distance between the lowest contact point on the superior surface of the tibial insert 82 at full extension to the bottom of the tibial tray 56 is between 10 mm to 24 mm and may vary in increments of 2 mm, though other suitable sizes may be used. This variation in thickness of the tibial insert 82 affords a surgeon sufficient variability to adjust the overall vertical dimensions of the knee joint prosthesis 10 to accommodate particular implantation. The tibial insert 82 is preferably machined or molded from a surgical grade, low-friction, low-wearing plastic, such as UHMWPE conforming to ASTM F 648 though other suitable materials may be used.

To provide second means for guiding movement of the femoral component, the tibial insert 82 includes a stabilizing post 88 which projects superiorly approximately 0.955 inch from the lowest articulating point on the superior surface 86 of the tibial insert 82. The stabilizing post 88 extends superiorly from the superior surface 86 of the tibial insert 82 and includes first and second laterally spaced-apart sides 90 and 92. The first and second sides 90 and 92 of the stabilizing post 88 are positioned so as to extend into the intercondylar recess 34 of the femoral component 18 and are dimensioned to satisfy rotational (4° of rotation) and varus-valgus (3° of varus-valgus angulation) constraints with respect to the first and second lateral sidewalls 36 and 38 of the intercondylar portion 32. In this regard, the distance between the first and second sides 90 and 92 is preferably 0.580 inch and is of relatively low tolerance. The edges of the first and second sides 90 and 92 of the stabilizing post 88 which met within the other surfaces of the stabilizing post 88 described below contain bevels 93.

The stabilizing post 88 further includes a posterior surface 94 as well as an anterior surface 96. The posterior surface 94 of the stabilizing post 88 extends in a substantially vertical direction with respect to the superior surface 86 of the tibial insert 82. The anterior surface 96 of the stabilizing post 88 projects superiorly in the posterior direction with respect to the superior surface 86 of the tibial insert 82 at an angle of approximately 120°. In addition, the anterior surface 96 of the stabilizing post 88 joins the superior surface 98 of the stabilizing post 88 at a rounded corner 100.

The stabilizing post 88 may or may not be reinforced. In the event that the stabilizing post 88 is reinforced, the tibial insert 82 has a bore 102 that extends from the superior surface 98 of the stabilizing post 88 to the inferior surface 84 of the tibial insert 82. Disposed within the bore 102 is a reinforcing pin 104 which is used to provide additional stability to the knee joint prosthesis 10 with respect to laterally imparted forces. The reinforcing pin 104 includes a head portion 106 which is operable to be received by a countersunk portion 108 of the bore 102. The countersunk portion 108 of the bore 102 is preferably deeper than the thickness of the head portion 106 of the reinforcing pin 104. The reinforcing pin 104 may preferably be made of Ti-6Al-4V, though other suitable materials may be used.

Disposed on the superior surface 86 of the tibial insert 82 is a first tibial bearing surface 110 and a second tibial bearing surface 112. The first and second tibial bearing surfaces 110 and 112 are dish-shaped in configuration. In this regard, the first and second tibial bearing surfaces 110 and 112 are each concavely curved in the coronal plane in a manner substantially similar to the first and second femoral bearing surfaces 28 and 30 of the femoral component 18. Accordingly, the area of contact between the first femoral bearing surface 28 and the first tibial bearing surface 110 represents a line rather than a point during a substantial portion of flexion if not entirely throughout flexion. Similarly, the area of contact between the second femoral bearing surface 30 and the second tibial bearing surface 112 also resembles a line during at least a substantial portion of flexion. This line-to-line contact in the coronal plane between at least a substantial portion of the femoral bearing surfaces 28 and 30 and the tibial bearing surfaces 110 and 112 reduces the stresses which occur between the femoral component 18 and the tibial insert 82 if the area of contact between the femoral bearing surfaces 28 and 30 and the tibial bearing surfaces 110 and 112 were point-to-point or less than complete line-to-line contact.

The first and second tibial bearing surfaces 110 and 112 each further includes a first and second articulating surfaces 114 and 116. The first and second articulating surfaces 114 and 116 are used to limit dislocation of the femoral component 18 in the sagittal plane with respect to the tibial component 22, and are located at the anterior and posterior portions of each of the first and second tibial bearing surfaces 110 and 112. Both the articulating surfaces 114 and 116 are concavely curved in the superior direction in the sagittal plane. In addition, the articulating surfaces 114 and 116 may be defined by two distinct radii of curvature in the sagittal plane, while the region between the articulating surfaces 114 and 116 in the sagittal plane is relatively planar and is sloped posteriorly by 3°.

The tibial insert 82 further includes a first and second vertical anterior recesses 118 and 120. The vertical anterior recesses 118 and 120 are located on the anterior portion of the tibial insert 82 and are adapted to receive the posts 62 and 64 of the tibial tray 56. In addition, the tibial insert 82 further includes a horizontal anterior recess 122. The horizontal anterior recess 122 is also disposed on the anterior portion of the tibial insert 82 and is operable to align with the horizontal posterior grooves 68 formed on the first and second posts 62 and 64 so as to receive a locking bar as described below.

The posterior surface of the tibial insert 82 has a horizontal posterior recess 126 adapted to receive the posterior projection 70 of the tibial tray 56 as shown in FIG. 4. The horizontal posterior recess 126 has a horizontal flange 128 which is adapted to be received in the horizontal channel 80 formed in the anterior surface of the posterior projection 70.

In order to attach the tibial insert 82 to the tibial tray 56, the surgeon places the tibial insert 82 on superior surface of the tibial tray 56 in a position slightly anterior with respect to the tibial tray 56. After the tibial insert 82 is located in this manner, the tibial insert 82 is pushed posteriorly causing the horizontal flange 128 on the posterior surface of the tibial insert 82 to engage the horizontal channel 80 of the posterior projection 70.

The tibial insert 82 is secured to the tibial tray 56 by means of a locking bar 132 as shown in FIG. 5. The locking bar 132 includes a main body 134 adapted to be received in the horizontal anterior recess 122 of the tibial insert 82 as well as the horizontal posterior grooves 68 formed on the first and second posts 62 and 64. The locking bar 132 includes a retaining portion 136, which upon full insertion, securely attaches to one of the posts 62 and 64 on the tibial tray 56 thereby securing the tibial insert 82 to the tibial tray 56. While the locking bar 132 is preferably made from Ti-6Al-4V, other suitable materials may be used.

The operation of the knee joint prosthesis 10 of the present invention will now be described with reference to FIGS. 6(a) through 6(e), which illustrate five different positions of the femoral component 18 with respect to tibial component 22, ranging from full extension in FIG. 6(a) to full flexion in FIG. 6(e). Reference will be made to Points C, D, and E which illustrate the various points on the tibial component 22 which contacts the femoral component 18 through the range of flexure.

In FIG. 6(a), the knee joint prosthesis 10, both anatomically and prosthetically, is inherently stable at full extension when the patient is standing. In this position, the first and second femoral bearing surfaces 28 and 30 of the femoral component 18 are nested within the first and second tibial bearing surfaces 110 and 112 of the tibial insert 82. The anterior surface 96 of the stabilizing post 88 and the anterior surface 40 of the intercondylar portion 32 do not necessarily engage. In addition, the cam portion 44 of the femoral component 18 does not engage the posterior surface 94 of the stabilizing post 88. If the knee joint should undergo a fairly large hyperextension (approximately 10°), the anterior surface 40 of the intercondylar portion 32 will engage the anterior surface 96 of the stabilizing post 88. In addition, the anterior surface 40 of the intercondylar portion 32 will engage the anterior surface 96 of the stabilizing post 88 to avoid posterior dislocation.

Motion of the femoral component 18 with respect to the tibial component 22 is most unrestricted between full extension, as illustrated in FIG. 6(a), and the point of flexion where the posterior surface 94 of the stabilizing post 88 and the cam portion 44 of the femoral component 18 initially engage as illustrated in FIG. 6(b).

This engagement generally occurs between 12° and 20° of flexion. Within this range, motion in the sagittal plane is restricted only in the sense that posterior dislocation of the femoral component 18 with respect to the tibial component 22 is prohibited at or near full extension by engagement of the anterior surface 96 of the stabilizing post 88 and anterior surface 40 of the intercondylar portion 32. Otherwise, the femoral component 18 is permitted to translate in the sagittal plane.

In particular, the femoral component 18 is able to undergo translation in the sagittal plane with respect to the tibial component 22 during this range of flexion. That is, the femoral component 18 is able to move anteriorly and posteriorly relatively freely with respect to the tibial component 22 while remaining in contact with the first and second tibial bearing surfaces 110 and 112. It will be appreciated that the exact amount of translation in the sagittal plane permitted by the knee joint prosthesis 10 will vary depending on the forces imparted by local soft tissues, muscles, tendons, ligaments as well as forces transmitted from the tibia and fibula. These forces will vary from patient to patient, from activity to activity, as well as from implantation to implantation.

When flexion exceeds approximately 12°-20° as shown in FIG. 6(b), the cam portion 44 of the femoral component 18 engages the posterior surface 94 of the stabilizing post 88. When the cam portion 44 and the posterior surface 94 of the stabilizing post 88 engage, the position of the contact area between the first and second femoral bearing surfaces 28 and 30 of the femoral component 18 and the first and second tibial bearing surfaces 110 and 112 of the tibial component 22 occurs at Point C and further anterior translation of the femoral component 18 with respect to the tibial component 22 is prohibited. As flexion continues, the femoral component 18 begins to rollback and slide with respect to the tibial component 22. As this happens, the position of the contact area at Point C of the tibial component 22 moves posteriorly in a direction toward Point D. The rollback is approximately proportional to the amount of flexion and continues until approximately 30° of flexion is reached as indicated in FIG. 6(c).

Between approximately 30° flexion as depicted in FIG. 6(c) and 90° flexion shown in FIG. 6(d), the first and second femoral bearing surfaces 28 and 30 slides with respect to the first and second tibial bearing surfaces 110 and 112. As this sliding movement occurs, the position of the contact area on the tibial component 22 where the femoral component 18 contacts the tibial component 22 remains substantially constant at Point D. The relatively constant position of the contact area between the femoral component 18 and the tibial component 22 is due to the interaction of the cam portion 44 of the femoral component 18 with the stabilizing post 88 of the tibial component 22. Because the position of the contact area on the tibial component 22 remains constant, the tibial insert 82 is not subject to the same wear characteristics as would be the case if the femoral component 18 was able to roll and slide with respect to the tibial component 22.

When flexion exceeds 90° as shown in FIG. 6(d), the femoral component 18 again undergoes rollback and sliding due to the interaction of the cam portion 44 of the femoral component 18 with the stabilizing post 88 of the tibial component 22. This rollback and sliding of the femoral component 18 with respect to the tibial component 22 continues until full flexion is reached at approximately 110° as indicated by FIG. 6(e). As this rollback and sliding occurs, the position of the contact area between the tibial component 22 and femoral component 18 and the shifts posteriorly from Point D to Point E.

The second embodiment of the present invention will now be described with reference to FIG. 7. Elements of the second embodiment which are similar to those of the first embodiment use similar reference numerals which are primed. The knee joint prosthesis 10' of the second embodiment is designed to provide adequate stability in cases of moderate deterioration and instability of the human knee, most typically when the anterior and posterior cruciate ligaments are sacrificed or dysfunctional and the medial and lateral collateral ligaments remain functionally intact. Functionally, the knee joint prosthesis 10' of the second embodiment differs from the knee joint prosthesis 10 of the first embodiment in that the second embodiment allows for more rotation around the superior-inferior axis (approximately ±15°) as well as permit relatively unlimited varus-valgus angulation. The femoral components associated with the second embodiment can either be universal or specifically designed for either the left knee or the right knee.

Structurally, the knee joint prosthesis 10' of the second embodiment is similar to the knee prosthesis 10 of the first embodiment with the exception of the intercondylar recess 34' of the femoral component 18' and the stabilizing post 88' of the tibial component 22'. In this regard, the anterior-posterior width of the stabilizing post 88' of the knee joint prosthesis 10' of the second embodiment is smaller than that of the knee joint prosthesis 10 of the first embodiment. Viewed anteriorly, the first and second sides 90' and 92' of the stabilizing post 88' diverge inferiorly. In addition, the first and second sides 90' and 92' diverge posteriorly in the sagittal plane. The first and second sides 90' and 92' converge in the superior direction and cause the stabilizing post 88' to taper in the superior direction. The height of the stabilizing post 88' of the second embodiment is shorter than the stabilizing post 88 of the first embodiment, extending approximately 0.838 inch from the lowest articulating point on the superior surface 86 of the tibial insert 82. Finally, there is no femoral stem boss associated with the knee joint prosthesis 10'.

The third embodiment of the present invention will now be described with reference to FIG. 8. Elements of the third embodiment which are similar to those of the first embodiment use similar reference numerals which are double-primed. The knee joint prosthesis 10" of the third embodiment is used for implantation into human knees having relatively minor disease and instability. The knee joint prosthesis 10" of the third embodiment would most typically be surgically implanted into a knee having the medial collateral, lateral collateral and posterior cruciate ligament functionally intact, and the anterior cruciate ligament sacrificed. The knee joint prosthesis of the third embodiment inherently provides the least amount of additional stability while providing the greatest relative amount of unconstrained motion. The femoral components associated with the third embodiment can either be universal or specifically designed for use with either the left knee or the right knee.

The femoral component 18" of the third embodiment comprises first and second condylar portions 24" and 26" which are interconnected by an intermediate portion 138 at the anterior portions of the first and second condylar portions 24" and 26". In addition, the femoral component 18" may or may not include distal instrument pegs 140 and 142. In the event that the femoral component 18" includes the distal instrument pegs 140 and 142, they are disposed on the superior surface of each of the condylar portions 24" and 26". The distal instrument pegs 140 and 142 are adapted to be surgically inserted into bores (not shown) formed by a surgeon in the distal end of a femur 14 which has been resected to aid in firmly attaching the femoral component 18 to the femur 14.

The tibial insert 82" of the third embodiment of the present invention includes the first and second tibial bearing surfaces 110" and 112" identical to those associated with the first two embodiments, but does not include a member similar to the stabilizing post 88. Further, the tibial insert 82" is provided with a relatively low convexly curved intercondylar eminence 144 disposed between the first and second tibial bearing surfaces 110" and 112". In addition, the surface equivalent to the articulating surface 114 is absent from the tibial insert 82". Finally, the tibial component 22" includes an inferiorly extending projection 146 which is able to be received by the boss of a support member as is well known in the art.

As implanted, the knee joint prosthesis 10" of the third embodiment relies to a greater extent upon functionally intact ligaments. The knee joint prosthesis 10" does not prevent the femoral component 18" from dislocating anteriorly or posteriorly. Rather, the functionally intact posterior cruciate and collateral ligaments ensure against such dislocation. In addition, the knee joint prosthesis 10" of the third embodiment provides for relatively free translation in the sagittal plane throughout substantially the entire range of flexion.

Without the stabilizing post 88 and the intercondylar portion 32 of the first embodiment, the knee joint prosthesis 10"of the third embodiment permits a greater degree of varus-valgus angulation. Furthermore, since the first and second femoral bearing surfaces 28" and 30" and the first and second tibial bearing surfaces 110" and 112" have a substantially constant radius of curvature in the coronal plane, line-to-line contact in the coronal plane is maintained during varus-valgus angulation.

It will be appreciated that knee joint prostheses of the present invention provides interchangeability between different sized femoral components and different sized tibial components. It will also be appreciated that the present invention is able to maintain line-to-line contact in the coronal plane between the femoral component and the tibial component during at least a substantial range of flexion as well as during varus-valgus angulation when such motion is permitted. In addition, it will also be appreciated that the femoral and tibial components can be interchanged while at the same time the tibial insert can be sized with the tibial tray so as to prevent underhang and overhang of the tibial insert with respect to the tibial tray. Further, the cam portion of the femoral component permits the extensor moment arm of the knee joint prosthesis to be proportional to the tibial component, while allowing the femoral component to have a relatively constant position of the contact area on the tibial component during a range of flexion. Finally, the knee joint prosthesis permits translation of the femoral component in the sagittal plane with respect to the tibial component during a range of flexion.

The foregoing discussion describes merely exemplary embodiments of the present invention. Those skilled in the art will appreciate the source of the components in the first, second and third embodiments may be interchanged with components of different embodiments to accommodate a particular implantation. The present invention may be used with conventional femoral and tibial augments so as to allow for bone deficiencies in the knee joint during a prosthetic implantation. The bearing surfaces on the femoral and tibial components may be formed from multiple radii of curvature in the coronal plane so long as the center-to-center distance of each radius is substantially constant for each size of femoral and tibial component. The tibial tray, tibial stem boss and non-articulating surfaces of the femoral component can be surface treated in order to increase porosity such as by use of a plasma spray. In addition, a surface treatment such as plasma nitriding may be used with the tibial component. One skilled in the art will readily recognize from such discussion, and from the accompanying drawings and claims, that various changes, modifications and variations can be made therein without departing from the spirit and scope of the invention as defined in the following claims.

What is claimed is:

1. A prosthetic replacement system for a knee having independently interchangeable components, comprising:
   a plurality of different sized femoral components each of which include
   (a) a first bearing surface having a cross-section in the coronal plane defined at least in part by a first radius, and
   (b) a second bearing surface having a cross-section in the coronal plane defined at least in part by a second radius, said second radius being displaced from said first radius, the distance between the center of said first radius to the center of said second radius being substantially equal for each of said femoral components; and
   a tibial component being able to operatively engage each of said femoral components;
   whereby one of said femoral components and said tibial component are used to provide a prosthetic replacement for the knee.

2. The prosthetic replacement system according to claim 1, wherein the distance between said first radius and said center of said first radius is substantially equal to the distance between said second radius and the center of said second radius.

3. The prosthetic replacement system according to claim 1, wherein said tibial component includes:
   (a) a first bearing surface having a cross-section in the coronal plane defined at least in part by said first radius; and
   (b) a second bearing surface having a cross-section in the coronal plane defined at least in part by said second radius.

4. The prosthetic replacement system according to claim 3, wherein the distance from said first radius to the center of said first radius is substantially equal to the distance from said second radius to the center of said second radius.

5. The prosthetic replacement system of claim 1, wherein said tibial component is operable to maintain line-to-line contact in the coronal plane with said first and second bearing surfaces of at least one of said femoral components during a substantial portion of flexion.

6. The prosthetic replacement system of claim 1, wherein said tibial component is operable to permit varus-valgus angulation of at least one of said femoral components, said tibial component being further operable to maintain line-to-line contact in the coronal plane with one of said bearing surfaces of said one femoral component during varus-valgus angulation.

7. The prosthetic replacement system of claim 1, wherein engagement of said tibial component with at least one of said femoral components is operable to permit translation in the sagittal plane of said one femoral component with respect to said tibial component during a portion of flexion.

8. The prosthetic replacement system of claim 1, wherein at least one of said femoral components includes means for maintaining the position of the contact area between said one femoral component and said tibial component substantially constant during a substantial portion of flexion.

9. The prosthetic replacement system according to claim 1, wherein each of said femoral components includes means for allowing movement of the contact area established by said tibial component and each of said femoral components during a portion of flexion to be substantially proportional to the size of the femoral component.

10. A prosthetic replacement system for a knee having independently interchangeable components, comprising:
   a plurality of different sized femoral components including
      a left femoral component comprising
         (a) a first bearing surface having a cross-section in the coronal plane defined at least in part by a first radius, and
         (b) a second bearing surface having a cross-section in the coronal plane defined at least in part by a second radius, said second radius being displaced from said first radius,
      a right femoral component comprising
         (a) a first bearing surface having a cross-section in the coronal plane defined at least in part by a first radius, and
         (b) a second bearing surface having a cross-section in the coronal plane defined at least in part by a second radius, said second radius being displaced from said first radius,
      the distance between the center of said first radius to the center of the second radius being substantially equal for each of said femoral components; and
   a tibial component being able to operatively engage each of said femoral components;
   whereby one of said femoral components and said tibial component are used to provide a prosthetic replacement for the knee.

* * * * *

UNITED STATES PATENT AND TRADEMARK OFFICE
CERTIFICATE OF CORRECTION

PATENT NO. : 5,330,534
DATED : July 19, 1994
INVENTOR(S) : Herrington, et al

It is certified that error appears in the above-indentified patent and that said Letters Patent is hereby corrected as shown below:

Column 6, line 59, "Conforming" should be --conforming--.

Column 6, line 59, "36" should be "136".

Column 13, line 28, Claim 1, "include" should be --includes--.

Signed and Sealed this

Twenty-seventh Day of June, 1995

Attest:

BRUCE LEHMAN

Attesting Officer

Commissioner of Patents and Trademarks